United States Patent
Biesel

(10) Patent No.: US 6,814,862 B2
(45) Date of Patent: Nov. 9, 2004

(54) METHOD AND APPARATUS FOR PROCESSING INTRA OR POSTOPERATIVE BLOOD LOSS FOR AUTOTRANSFUSION

(75) Inventor: Wolgang Biesel, Ottweiler (DE)

(73) Assignee: Fresenius AG, Bad Homburg (DE)

( * ) Notice: Subject to any disclaimer, the term of this patent is extended or adjusted under 35 U.S.C. 154(b) by 163 days.

(21) Appl. No.: 09/922,888

(22) Filed: Aug. 6, 2001

(65) Prior Publication Data

US 2002/0011453 A1 Jan. 31, 2002

Related U.S. Application Data

(62) Division of application No. 09/235,964, filed on Jan. 22, 1999, now Pat. No. 6,299,784.

(30) Foreign Application Priority Data

Jan. 23, 1998 (DE) .......................... 198 02 321

(51) Int. Cl.⁷ .......................... B01D 36/00; B04B 11/00
(52) U.S. Cl. .................. 210/258; 210/252; 210/257.1; 210/134; 210/143; 494/35; 494/43
(58) Field of Search ................ 210/134, 143, 210/252, 257.1, 258; 494/35, 43, 45; 604/4.01, 5.01, 6.01, 6.11, 6.02

(56) References Cited

U.S. PATENT DOCUMENTS

| 3,655,123 | A | * | 4/1972 | Judson et al. | |
|---|---|---|---|---|---|
| 4,014,329 | A |   | 3/1977 | Welch et al. | |
| 4,187,979 | A | * | 2/1980 | Cullis et al. | 210/782 |
| 4,416,654 | A | * | 11/1983 | Schoendorfer et al. | 494/10 |
| 4,804,363 | A | * | 2/1989 | Valeri | 210/782 |
| 4,826,811 | A | * | 5/1989 | Sehgal et al. | 514/6 |
| 4,879,031 | A | * | 11/1989 | Panzani | 210/364 |
| 4,886,487 | A |   | 12/1989 | Solem et al. | |
| 4,911,833 | A | * | 3/1990 | Schoendorfer et al. | 210/782 |
| 5,034,135 | A | * | 7/1991 | Fischel | 210/651 |
| 5,147,290 | A | * | 9/1992 | Jonsson | 494/27 |
| 5,234,403 | A | * | 8/1993 | Yoda et al. | 210/650 |
| 5,298,171 | A | * | 3/1994 | Biesel | 210/739 |
| 5,419,759 | A | * | 5/1995 | Naficy | 210/764 |
| 5,445,593 | A | * | 8/1995 | Biesel et al. | 494/43 |
| 5,971,948 | A | * | 10/1999 | Pages et al. | 210/645 |

FOREIGN PATENT DOCUMENTS

| DE | 2262856 | 8/1973 |
|---|---|---|
| DE | 3817664 | 11/1989 |
| DE | 4226974 | 2/1994 |
| EP | 0 155 684 | 9/1985 |
| EP | 0 303 765 | 2/1989 |
| WO | WO 89/01792 | 3/1989 |

\* cited by examiner

Primary Examiner—John Kim
(74) Attorney, Agent, or Firm—Kenyon & Kenyon

(57) ABSTRACT

A method and an apparatus for continuous processing of intra- or postoperative blood loss for autotransfusion. According to the present invention, certain cells of the cell suspension to be processed, mainly the red blood cells, are concentrated by centrifuging in a separation unit and removed from the separation unit without being rinsed or washed in the separation unit. The concentrated cell fraction is diluted with a physiological solution, preferably a Ringer's solution, after being removed from the separation unit.

15 Claims, 2 Drawing Sheets

METHOD AND APPARATUS FOR PROCESSING INTRA OR POSTOPERATIVE BLOOD LOSS FOR AUTOTRANSFUSION

CROSS-REFERENCE TO RELATED APPLICATION

This application is a division of U.S. patent application Ser. No. 09/235,964, filed on Jan. 22, 1999, now U.S. Pat. No. 6,299,784.

FIELD OF THE INVENTION

The present invention relates to a method of processing intra- or postoperative blood loss for autotransfusion, where certain cells of the cell suspension to be processed are concentrated by centrifugation in a separation unit and then removed from the separation unit. In addition, the present invention concerns an apparatus for carrying out such a method. The related art describes various separation devices and the respective methods, where blood in particular is separated into its components, and the latter, such as red blood cells or plasma, are forwarded for further use.

BACKGROUND OF THE INVENTION

There are various medical applications for such methods and equipment. One of these applications is for intraoperative autotransfusion, which has been widely used in recent times. Intraoperative autotransfusion is a method which permits retransfusion of blood collected from the surgical field. What are known as whole-blood transfusion methods, which subject the collected blood to particle filtration only, are used in the area of intraoperative autotransfusion to the point of plasma separation/washing methods which supply a washed RBC concentrate for reinfusion. The advantages of transfusion of autologous blood, i.e., the patient's own blood, in comparison with transfusion of homologous blood, i.e., someone else's blood, include the prevention of infectious diseases such as AIDS and hepatitis as well as the prevention of transfusion reactions due to biological incompatibility and immune system reactions.

As part of the development of intraoperative autotransfusion techniques, it has been found that transfusion of whole blood may be a disadvantage in comparison with transfusion of washed RBC concentrates. These disadvantages of the whole blood transfusion methods include the fact that undesirable components of the collected blood cannot be eliminated. Intraoperative blood contains unknown quantities of hemolysis products, foreign constituents infiltrated from the tissue or from external sources, excess volume, anticoagulants, activated plasma and cellular coagulation factors, products of the activation of coagulation and products of the fibrinolytic system. All these components can cause clinical complications, which has led to restrictions on the scope of use. It is known from the related art that blood filtering systems can be used with such autotransfusion systems, but these filters retain only blood clots or pieces of tissue. Such a system is known from U.S. Pat. No. 4,014,329. U.S. Pat. No. 4,886,487 describes an apparatus for separating excess fluids, but coagulation factors, washing fluid, anticoagulants and other additives are returned with the patient's blood.

As an alternative to whole-blood transfusion, phase separation/washing methods using centrifuges have been developed. Such centrifuges are described in Unexamined German Patent No. 2,262,856 and International Patent WO 89/01792.

German Patent No. 3,817,664 describes a countercurrent extraction centrifuge, in which whole blood is carried in countercurrent with a wash solution. However, neither this apparatus nor this method meets the requirements demanded for autotransfusion, because the unwanted components cannot be separated reliably and effectively.

German Patent No. 4,226,974 C2 describes a method of processing intraoperative blood loss, in which the cell suspension to be processed is passed through a centrifuge line into a separation chamber, where it is broken down into its components according to density. In a second process step, the concentrated cell fraction, mainly RBC concentrate, is resuspended by continuous addition of a wash solution. Then the remaining noncellular components are subjected to another separation, yielding a high-purity RBC concentrate after removal of the contaminated wash solution. A centrifuge with a separation chamber having an annular channel is used to carry out the process. The annular channel is divided into three zones, with the first separation of the cell suspension taking place in the first zone, resuspension in the second zone and the second separation of the resuspended cells in the third zone.

The above method has proven successful in practice, but it has the disadvantage that relatively large volumes of wash solution must be passed through the centrifuge chamber to displace or dilute the remaining plasma. In view of the large volumes, an isotonic saline solution is generally used as the wash solution in the known method. Because of the relatively large volumes involved, using Ringer's solution, which is tolerated much better by the patient, instead of saline solution is associated with a relatively high cost because the Ringer's solution is more expensive.

OBJECT OF THE INVENTION

The object of the present invention is to provide a method for processing intra- or postoperative blood loss for autotransfusion, making it possible to obtain a highly pure concentrate by using only small volumes of a dilution solution. This object is achieved with a method for processing a cell suspension for autotransfusion comprising the steps of centrifuging the suspension in a separation unit, removing the concentrated cells from the separation unit, and diluting the concentrated cells with a physiological solution.

Another object of the present invention is to make available an apparatus for carrying out the method of processing intra- or postoperative blood loss for autotransfusion. This object is achieved with a device for processing red blood cell suspensions for autotransfusion comprising one or more separation units disposed in a centrifuge, wherein the separation unit has a suspension inlet line, a red blood cell outlet line and a waste line, wherein the red blood cell outlet line is connected to a diluting device. According to the invention, a red blood cell suspension enters the separation unit through the inlet line and is concentrated in the separation unit. The concentrated red blood cells are then removed through the red blood cell outlet line where they are diluted with a physiologic solution.

The method of processing a cell suspension for autotransfusion according to the present invention, especially for continuous processing of intra- or postoperative blood loss to yield an RBC concentrate for the purpose of returning it to the patient, is based on the fact that autotransfusion is performed without rinsing or washing the concentrated cells again. With the method according to the present invention, certain cells of the prepared cell suspension, mainly the red blood cells, are concentrated by centrifuging in a separation unit and are removed from the separation unit without washing or rinsing the concentrated cells in the separation unit. Surprisingly, it has been found that separation is not only much faster but is also more effective inasmuch as the cell concentrate obtained, in particular the RBC concentrate, has a greater purity, i.e., less contamination with white blood cells.

Only small volumes of a dilution solution are necessary to dilute the cell concentrate thus obtained. Therefore, using Ringer's solution, which is tolerated much better by the patient than saline solution, is not associated with much higher costs. Instead of Ringer's solution, however, the cell concentrate may also be diluted with stock solutions for blood cells, etc.

It is also advantageous that the desired hematocrit of the end product can be adjusted freely by selecting the dilution ratio. This also avoids large volumes of waste contaminated with blood components. Extraction of red blood cells is very efficient because there is no cell loss in a washing operation. The plasma components of the blood can be collected undiluted for further use.

The apparatus for carrying out the method according to the present invention has a simplified design inasmuch as no separate inlet line for a wash solution is needed on the separation unit. Thus, the separation unit, which is preferably designed as a disposable unit, may be manufactured inexpensively. The cell concentrate is preferably diluted immediately after removal from the separation unit. In a preferred embodiment of the apparatus according to the present invention, the device for dilution of the cell fraction removed from the separation unit has a container to accommodate the physiological dilution solution and an inlet line leading away from the container and opening into the outlet line for the concentrated cell fraction. The mixing point where the inlet line for the dilution solution opens into the outlet line for the cell concentrate is preferably located upstream from the delivery pump by means of which the cell fraction is removed from the separation unit. This minimizes hemolysis effects due to high cell concentration and shearing forces. To be able to freely select the hematocrit of the end product, the dilution device has a control unit which can adjust the delivery rate of the pump for supplying the dilution solution. The present invention is explained in greater detail below on the basis of one embodiment with reference to the drawings.

DETAILED DESCRIPTION OF THE PREFERRED EMBODIMENT

Figure 1:
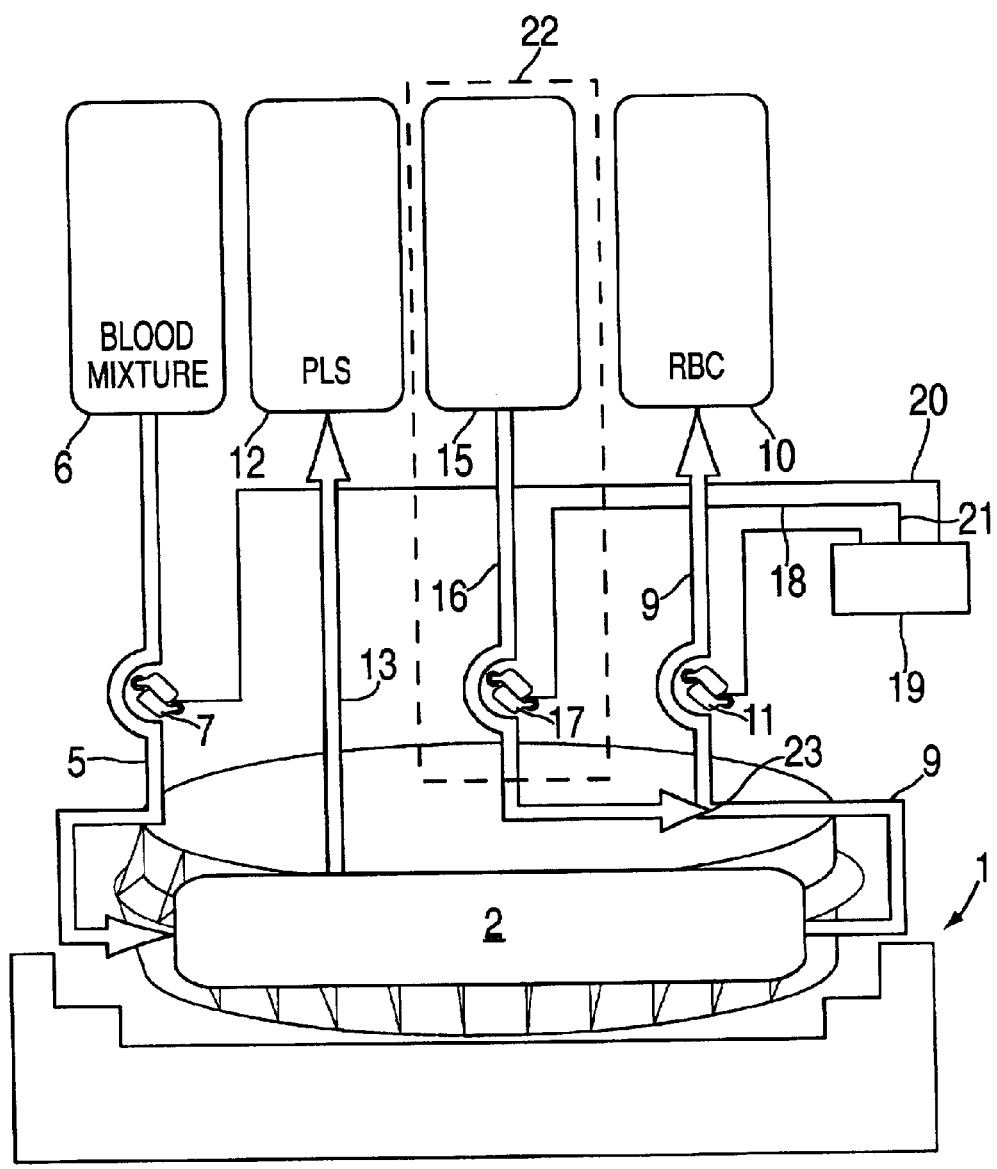
FIG. 1: a simplified schematic diagram of an embodiment of the apparatus according to the present invention for processing intra- or postoperative blood loss for autotransfusion.

The apparatus includes a centrifuge 1 with a centrifuge chamber 2 designed as a disposable unit which is inserted into the centrifuge. These parts are only alluded to in FIG. 1.

Figure 2:
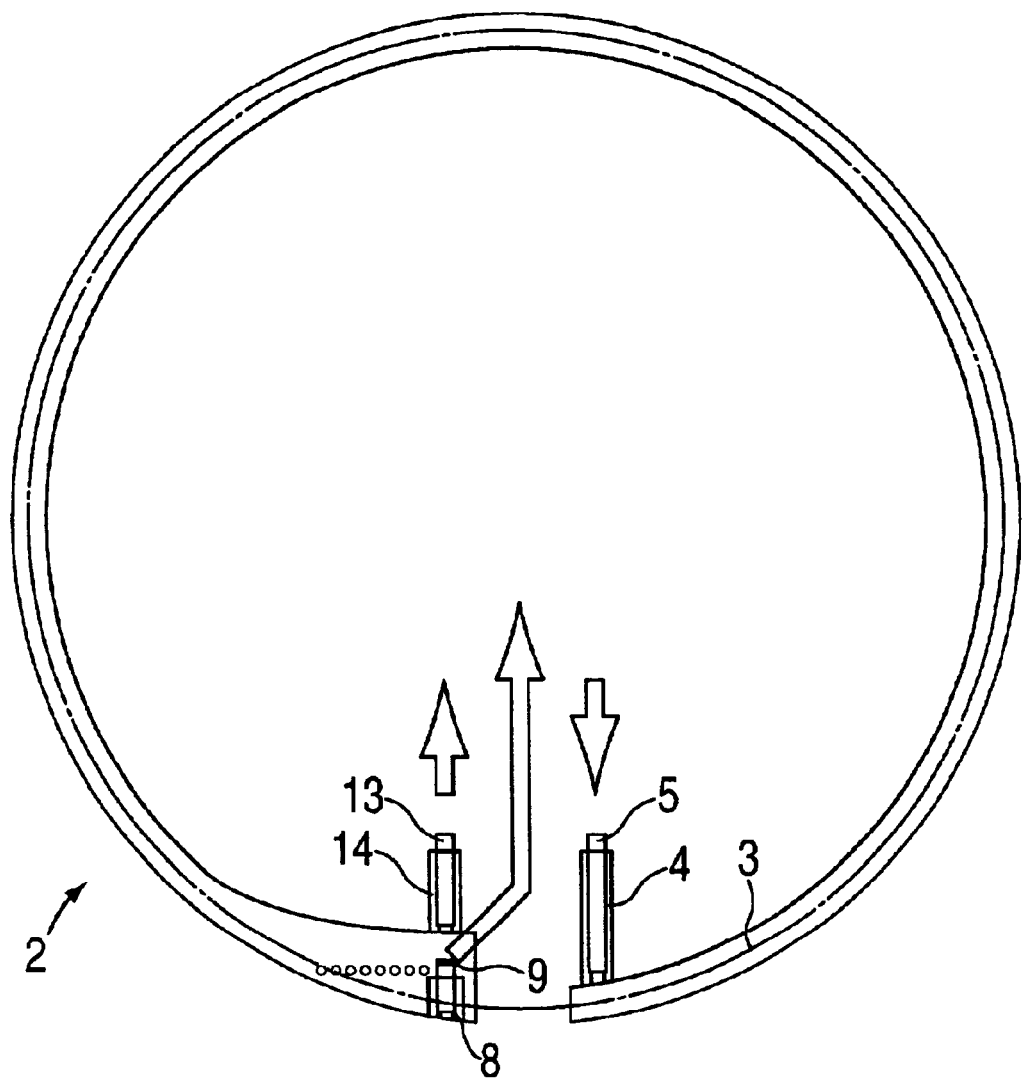
FIG. 2: a simplified schematic diagram of the separation unit of the apparatus for carrying out the process from FIG. 1.

Centrifuge chamber 2 has an annular channel 3 (FIG. 2). Provided on the inside of the narrow end of the annular channel is a connection 4 to which is connected an inlet line 5 for supplying the cell suspension to be processed, which comes from a container 6 holding a patient's blood mixture collected during or after surgery. An occluding blood pump 7 is connected to inlet line 5.

Provided on the outside of the end of the annular channel there is a connection 8 to which is connected a first outlet line 9 for the concentrated cell fraction, i.e., the RBC concentrate (RBC) leading to a collecting tank 10. An occluding concentrate pump 11 is connected to the first outlet line 9.

A second outlet line 13 for unwanted components (plasma, PLS) leading to another collecting tank 12 is connected to a connection 14 of the separation chamber provided on the inside of annular channel 3.

During operation of the apparatus, the blood mixture to be processed is delivered by blood pump 7 to rotating separation chamber 2, in whose annular channel 3 the whole blood is separated under the effect of centrifugal force, with the red blood cells settling on the outside of the annular channel and being removed continuously from the separation chamber by concentrate pump 11 through the first outlet line 9 and collected in tank 10. However, unneeded components (tissue fluid/plasma) of the blood mixture are removed continuously through the second outlet line 13 and collected in tank 12.

The apparatus according to the present invention also has a device 22 for diluting the RBC concentrate removed through the first outlet line 9. Dilution device 22 includes a tank 15 to hold the dilution solution, preferably Ringer's solution, with an inlet line 16 leading away from it and opening into the first outlet line 9 upstream from concentrate pump 11 at a mixing point 23. An occluding delivery pump 17 connected to inlet line 16 is also connected to a central control unit 19 by a control line 18. Control unit 19 is also connected to blood pump 7 and concentrate pump 11 by additional control lines 20, 21. The delivery rates of pumps 7, 11, 17 can be set by the control unit. The desired hematocrit of the RBC concentrate to be returned to the patient can be preset by appropriate adjustment of the delivery rate of pump 17 or pump 11.

The blood mixture is separated to a hematocrit of 60 to 98, preferably 85, in separation chamber 2, which may be designed in the shape of a ring or a spiral.

The following table shows the plasma and WBC elimination rates that can be achieved with the method according to the present invention at a hematocrit of the blood of 20% and a hematocrit of the RBC concentrate of 70%, 80% and 90%.

| Hct (blood) (%) | Hct (RBC concentrate) (%) | Plasma elimination (%) | WBC elimination (%) |
|---|---|---|---|
| 20 | 70 | 89 | approx. 80 |
| 20 | 80 | 94 | approx. 90 |
| 20 | 90 | 97 | >90 |

What is claimed is:

1. A device for processing cell suspensions for autotransfusion comprising at least one separation unit for separating cells by centrifugation, the separation unit comprising a suspension inlet line and a concentrated cell outlet line having a concentrated cell outlet pump under the control of a controller and a waste line each located downstream of the suspension inlet line, the concentrated cell outlet line being connected to a diluting device, the diluting device being in fluid connection with the concentrated cell outlet line via a solution line for delivering physiologic solution, wherein the solution line is connected to the concentrated cell outlet line upstream of the concentrated cell outlet pump, wherein cells contained in a suspension entering the separation unit through the inlet line under the control of the controller are concentrated in the separation unit, removed through the concentrated cell outlet line, and diluted via the diluting device with a physiologic solution.

2. The device of claim 1, wherein the remainder of the suspension separated from the cells is removed from the separation unit through the waste line.

3. The device of claim 1, wherein the solution line has a solution pump for controlling the flow of physiologic solution.

4. A device for processing cell suspensions for autotransfusion comprising at least one separation unit for separating cells by centrifugation, the separation unit comprising a suspension inlet line and a concentrated cell outlet line and a waste line each located downstream of the suspension inlet line, the concentrated cell outlet line being connected to a diluting device, the dilution device being in fluid connection with the concentrated cell outlet line via a solution line for delivering physiologic solution, wherein cells contained in a suspension entering the separation unit through the inlet line are concentrated in the separation unit, removed through the concentrated cell outlet line, and diluted via the diluting device with a physiologic solution, wherein the solution line has a solution pump for controlling the flow of physiologic solution and wherein the concentrated cell outlet line has a concentrated cell pump for controlling the flow of concentrated cells from the separation unit, the solution line being connected to the concentrated cell outlet line upstream of the concentrated cell pump.

5. The device of claim 4, further comprising control means, connected to the concentrated cell pump and solution pump, for controlling the flow of concentrated cells and physiologic solution.

6. The device of claim 5, wherein the control means, controls a rate of delivery of at least one of the concentrated cell pump and the solution pump so as to concentrate red blood cells to a hematocrit of 60 to 98 percent.

7. The device of claim 5, wherein the control means controls a rate of delivery of at least one of the concentrated cell pump and the solution pump so as to concentrate red blood cells to a hematocrit of 85 percent.

8. The device of claim 5, wherein the control means controls the concentration of the diluted cells.

9. The device of claim 1, wherein the separation unit has a shape selected from the group consisting of a ring and a spiral.

10. The device of claim 1, wherein the separation unit further comprises a channel located between the suspension inlet and the concentrated cell outlet.

11. The device of claim 1, wherein the device processes cell suspensions collected intraoperatively.

12. The device of claim 1, wherein the device processes cell suspensions collected post-operatively.

13. A device for processing a suspension containing red blood cells for autotransfusion comprising at least one separation unit for concentrating red blood cells by centrifugation, the separation unit comprising a suspension inlet connected to a suspension inlet line having a suspension pump, a red blood cell outlet connected to a red blood cell outlet line having a red blood cell pump, and a waste outlet connected to a waste outlet line;

a dilution device comprising a physiologic solution tank and a solution line having a solution pump, the solution line providing fluid connection between the physiologic solution tank and the red blood cell outlet line, the connection between the solution line and the red blood cell outlet line being upstream of the red blood cell pump; and a control unit connected to the red blood cell pump and solution pump, wherein the control unit controls the flow and mixing rate of concentrated red blood cells and physiologic solution;

wherein red blood cells contained in a suspension entering the separation unit through the suspension inlet are concentrated in an annular channel of the separation unit, removed through the red blood cell outlet line, and diluted with physiologic solution.

14. The device of claim 13, wherein the remainder of the suspension is removed through the waste line.

15. The device of claim 13, wherein the control unit controls a rate of delivery of at least one of the red blood cell pump and the solution pump so as to concentrate the red blood cells to a hematocrit of 60 to 98 percent.

* * * * *